United States Patent
Wolf et al.

(10) Patent No.: US 11,331,071 B2
(45) Date of Patent: May 17, 2022

(54) SYSTEMS, METHODS, AND STRUCTURES FOR PULMONARY VEIN ISOLATION LESION EVALUATION

(71) Applicant: Duke University, Durham, NC (US)

(72) Inventors: Patrick Wolf, Durham, NC (US); Daniel Friedman, Durham, NC (US); Peter Hollender, Durham, NC (US); Tristram Bahnson, Durham, NC (US)

(73) Assignee: Duke University, Durham, NC (US)

( * ) Notice: Subject to any disclaimer, the term of this patent is extended or adjusted under 35 U.S.C. 154(b) by 738 days.

(21) Appl. No.: 16/052,251

(22) Filed: Aug. 1, 2018

(65) Prior Publication Data

US 2019/0038254 A1  Feb. 7, 2019

Related U.S. Application Data

(60) Provisional application No. 62/539,590, filed on Aug. 1, 2017.

(51) Int. Cl.
| | |
|---|---|
| *A61B 8/00* | (2006.01) |
| *A61B 8/08* | (2006.01) |
| *A61B 18/14* | (2006.01) |
| *A61B 5/00* | (2006.01) |
| *A61M 25/10* | (2013.01) |
| *A61B 90/00* | (2016.01) |
| *A61B 18/00* | (2006.01) |
| *A61B 6/00* | (2006.01) |
| *A61B 5/02* | (2006.01) |

(52) U.S. Cl.
CPC .............. *A61B 8/085* (2013.01); *A61B 8/485* (2013.01); *A61B 18/1492* (2013.01); *A61B 5/0095* (2013.01); *A61B 5/02007* (2013.01); *A61B 5/4836* (2013.01); *A61B 5/6853* (2013.01); *A61B 6/504* (2013.01); *A61B 90/37* (2016.02); *A61B 2018/0022* (2013.01); *A61B 2018/00577* (2013.01); *A61B 2018/00982* (2013.01); *A61B 2090/3784* (2016.02); *A61M 25/10* (2013.01)

(58) Field of Classification Search
CPC ..... A61B 8/085; A61B 18/1492; A61B 8/485; A61B 2018/00982; A61B 6/504; A61B 2090/3784; A61B 2018/00577; A61B 5/6853; A61B 5/0095; A61B 5/02007; A61B 5/4836; A61B 90/37; A61B 2018/0022; A61M 25/10
See application file for complete search history.

(56) References Cited

U.S. PATENT DOCUMENTS

| | | | | |
|---|---|---|---|---|
| 6,004,269 | A  * | 12/1999 | Crowley | A61B 8/4461 |
| | | | | 600/374 |
| 10,123,903 | B2 * | 11/2018 | Warnking | A61F 7/02 |
| 2008/0234661 | A1 * | 9/2008 | Hastings | A61M 25/0009 |
| | | | | 604/528 |
| 2012/0209116 | A1 * | 8/2012 | Hossack | A61B 8/481 |
| | | | | 600/439 |
| 2013/0211436 | A1 * | 8/2013 | Larson | A61N 7/022 |
| | | | | 606/169 |

(Continued)

*Primary Examiner* — Joel Lamprecht
(74) *Attorney, Agent, or Firm* — Kaplan Breyer Schwarz, LLP

(57) ABSTRACT

Aspects of the present disclosure describe systems, methods, and structures for pulmonary vein isolation lesion evaluation that advantageously determine lesion durability.

21 Claims, 10 Drawing Sheets

(56) References Cited

U.S. PATENT DOCUMENTS

2014/0350401 A1* 11/2014 Sinelnikov ......... A61B 17/2202
  600/439
2015/0272548 A1* 10/2015 Lu ....................... A61B 8/4488
  600/447

* cited by examiner

SYSTEMS, METHODS, AND STRUCTURES FOR PULMONARY VEIN ISOLATION LESION EVALUATION

CROSS REFERENCE TO RELATED APPLICATION

This application claims the benefit of U.S. Provisional Patent Application Ser. No. 62/539,590 filed 1 Aug. 2017 the entire content of which is incorporated by reference as if set forth at length herein.

TECHNICAL FIELD

This disclosure relates generally to medical imaging and instrumentation and in particular to systems, methods, and structures for pulmonary vein isolation lesion evaluation.

BACKGROUND

Percutaneous catheter ablation for atrial fibrillation (AF) is one of the most commonly performed therapeutic ablation procedures with more than 50,000 procedures performed annually in the United States alone. As is known, a desired therapeutic result of left atrial (LA) ablation for AF is pulmonary vein isolation (PVI) resulting from contiguous transmural ablation lesions formed around pulmonary vein (PV) ostia which in turn electrically isolate the PV musculature from the LA.

Presently, PVI is confirmed by demonstrating acute conduction block into and out of the PV's using a circular mapping catheter or high-density voltage mapping. Despite PVI therapeutic success however, less than 60-80% of PVI procedures achieve a 5-year success rate. When patients undergo a repeat ablation, PV reconnection due to conducting gaps in regions of previous ablation(s) are seen in a high percentage of veins. Accordingly, while acute PVI is necessarily performed, an uncertainty remains with respect to PVI durability. One reason for the uncertainty is an inability in the art to distinguish between durable tissue destruction and incomplete ablation resulting in injured, non-conducting tissue destined to heal and recover over time.

SUMMARY

The above problem is solved and an advance in the art is made according to aspects of the present disclosure directed to systems, methods, and structures for pulmonary vein isolation lesion evaluation.

In sharp contrast to the prior art which employed electrical isolation measurements, systems, methods, and structures according to the present disclosure advantageously provide information indicative of the durability of the isolation lesion.

According to certain aspects of the present disclosure an imaging catheter structure for isolation lesion evaluation includes an imaging catheter; a balloon affixed to a distal end of the catheter that anchors the catheter to surrounding tissue upon inflation; and an impulse generator in mechanical communication with the balloon configured such that when the impulse generator is active, mechanical impulses are conducted to the isolation lesion via the balloon.

BRIEF DESCRIPTION OF THE DRAWING

A more complete understanding of the present disclosure may be realized by reference to the accompanying drawing in which.

Figure 1A:
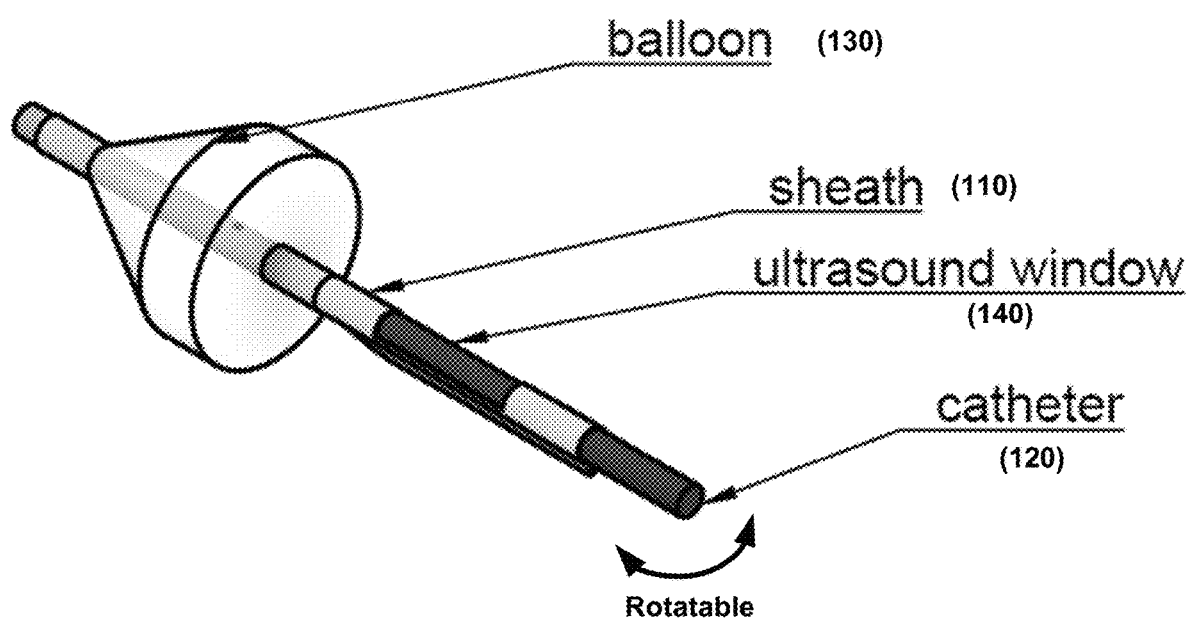
FIGS. 1(A), 1(B), and 1(C) are schematic diagrams of an illustrative imaging catheter arrangement for lesion evaluation according to aspects of the present disclosure.

The illustrative embodiments are described more fully by the Figures and detailed description. Embodiments according to this disclosure may, however, be embodied in various forms and are not limited to specific or illustrative embodiments described in the drawing and detailed description.

DESCRIPTION

The following merely illustrates the principles of the disclosure. It will thus be appreciated that those skilled in the art will be able to devise various arrangements which, although not explicitly described or shown herein, embody the principles of the disclosure and are included within its spirit and scope.

Furthermore, all examples and conditional language recited herein are intended to be only for pedagogical purposes to aid the reader in understanding the principles of the disclosure and the concepts contributed by the inventor(s) to furthering the art and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Thus, for example, it will be appreciated by those skilled in the art that any block diagrams herein represent conceptual views of illustrative circuitry embodying the principles of the disclosure.

Unless otherwise explicitly specified herein, the FIGs comprising the drawing are not drawn to scale.

By way of some additional background, we begin by noting that atrial fibrillation (AF) has been estimated to afflict more than 2.3 million individuals in the United States alone and its prevalence will likely increase to more than double that number by 2050. As will be readily appreciated, atrial fibrillation produces significant symptoms, negatively impacts quality of life, and is independently associated with adverse health effects such as mortality, stroke, cognitive decline, and worsening heart failure outcomes. Furthermore, the need for hospitalization and healthcare costs associated with treating atrial fibrillation are significant—as AF remains the most common arrhythmia requiring acute hospitalization.

Those skilled in the art will readily understand that drug therapy for AF is oftentimes ineffective and has not been shown to improve mortality rates.

Catheter ablation using radiofrequency energy (RFA) has been shown to improve quality of life and reduce hospitalization in the AF patient population. Consequently, RFA has emerged as an important new therapy option and is oftentimes recommended for patients with paroxysmal AF as a primary or secondary therapy option—or for other forms of AF when drug therapy has failed. Accordingly, RFA for AF (RFA-AF) has become a commonly performed ablation procedure for arrhythmias in the United States and—desirably—may also reduce mortality and strokes in patients undergoing such treatment.

Those skilled in the art will further appreciate that a primary acute therapy goal of RFA-AF is to produce conduction block(s) between the pulmonary vein (PV) musculature and the atria—known in the art as PV isolation (PVI)—because AF initiation is believed to originate in most patients from these regions of the heart. Unfortunately, the acute and long-term success of RFA-AF has been limited due—in part—to the recovery across previously ablated regions leading to PV reconnection even after repeat procedures.

To date, lesion assessment during RFA-AF procedures has generally involved demonstrating conduction block across a targeted region or demonstrating the inability to pace-capture the targeted region.

However—as those skilled in the art will readily understand—these methods are an indirect measure of lesion formation and describe tissue function and excitability and may not distinguish between injured tissue that is temporarily not excitable—but destined to recover—from "durable" or more-permanent lesions.

Accordingly, systems, methods, and structures that facilitate the assessment of acute lesion delivery and more reliably assess the completeness and durability of delivered RFA lesions—particularly acutely and intra-procedurally—would be a welcome addition to the art and be expected to greatly improve the long-term success of RFA-AF.

Acoustic radiation force impulse (ARFI) imaging is an ultrasound technique that images tissue elasticity. As with B-mode images—two-dimensional ultrasound image displays wherein bright dots represent ultrasound echoes—an ARFI is created as a series of lines but pixels in each line indicate displacement instead of brightness. Operationally—to start a line sequence—several imaging pulses are used to track the intrinsic tissue movement using speckle tracking, a high intensity "push" pulse is used to displace the tissue and several more imaging pulses are used to track the displacement resulting from the push.

A motion filter is used to subtract any intrinsic motion resulting in a induced displacement measurement. This high-resolution displacement information is superimposed in color on the B-mode images. Image pixels that represent stiff tissue show smaller displacements than more elastic tissue. Advantageously, each image only requires approximately 80 ms to generate.

As those skilled in the art will readily appreciate, ARFI imaging can: 1) identify circumscribed RFA lesions that correlate with histologically proved lesions; 2) allow visualization of RFA lesion formation in vivo; 3) can be adapted to an existing intra-cardiac ultrasound imaging system to obtain intra-procedural images during RFA; 4) can distinguish between an incomplete atrial ablation line containing a conducting gap versus a complete ablation line with conduction block; and 5) identifies intra-procedural acute and chronic gaps in RFA lesion sets during repeat ablation for atrial flutter and chronic gaps at the site of any PV reconnection during repeat RFA-AF.

These observations—taken together with the fact that intra-cardiac ultrasound is used by nearly all clinical centers during therapeutic RFA-AF, provides support for the thesis that ARFI imaging is well suited as a lesion assessment and endpoint determination technique as it directly reveals the extent of irreversible thermo-coagulation necrosis and durable RFA lesions—in vivo.

Despite such utility however, contemporary two-dimensional intra-cardiac ultrasound catheters only allow for a narrow field of view and small imaging distances when used for ARFI imaging. This significantly limits interrogation of all PV antral ablation sites during clinical evaluation. Advantageously, systems, methods and structures according to certain aspects of the present disclosure overcome this—and other—shortcomings of the art.

Figure 1B:
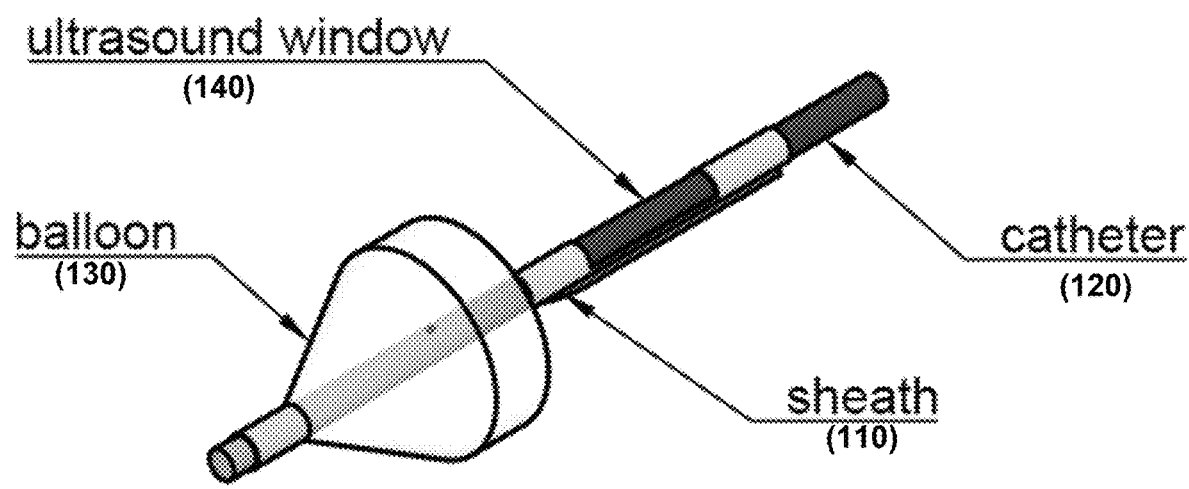
Figure 1C:
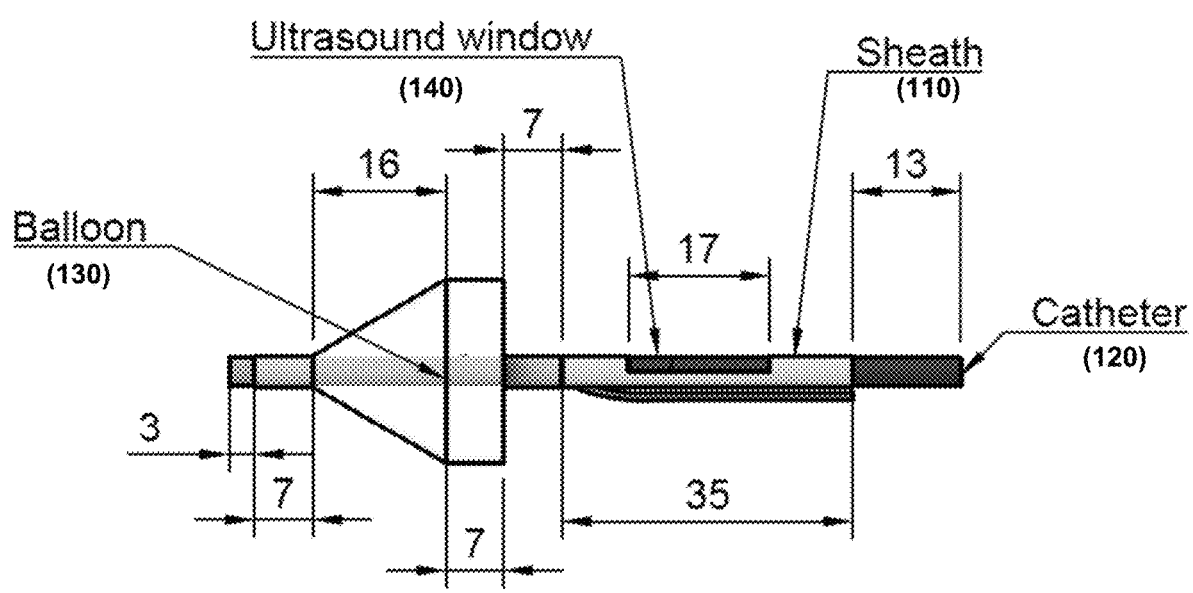

With simultaneous reference now to FIGS. 1(A), 1(B), and 1(C), there is shown schematic diagram(s) of an illustrative imaging catheter arrangement that—advantageously—may be employed to facilitate elasticity imaging for lesion evaluation according to the present disclosure. As may be observed from that figure, the catheter arrangement 100 includes an imaging catheter 120 positioned within a sheath 110 and having an inflatable balloon positioned at an end of the sheath—distal to the imaging catheter. Shown formed in a portion of the sheath is an ultrasound window at a location of the sheath that substantially corresponds to ultrasound imaging structures of the catheter—not specifically shown. Those skilled in the art will appreciate that the imaging window and catheter imaging structure(s) are located such that they permit ultrasonic interrogation of any lesion(s) that are situated in the left atria pulmonary vein ostia that may have been formed—for example—by an ablation procedure.

As will be readily appreciated by those skilled in the art, the length(s) of the sheath and the catheter are such that they may inserted/directed and positioned in desirable locations in the human heart and in particular in the left atrial pulmonary vein. Accordingly, during a lesion evaluation session, the sheath/catheter arrangement is inserted into a patient (for example, via femoral vessel) and directed to the left atrial pulmonary vein. Once so positioned, the balloon is inflated thereby anchoring the sheath in place.

At this point we note that the "inflation" of the balloon is preferably done with a biocompatible liquid such as sterile saline or other liquid solution. As we shall show and describe, such liquid—while being biocompatible—provides further advantage as such liquid provides an effective medium for conduction of any shock/pressure pulse/wave used to excite the lesion tissues.

Upon anchoring, a pressure pulse may be generated—and as we shall show and describe—either externally to the balloon or internally to the balloon—wherein the pulse will conduct through the tissue and subsequently detected via the ultrasonic imaging probe. Advantageously, pressure pulses according to the present disclosure may be of a particular frequency or over a range of frequencies—i.e., 300-500 Hz to the balloon and conducted to tissues is suitable for ultrasonic imaging applications such as those shown and described herein.

As noted previously, such ultrasonic imaging provides a "line" of interrogation with respect to the imaged tissue. Consequently, repeated lines of image(s) are collected at different rotational positions relative to one another until a desired (for example—full 360 degree) set of images are collected for the lesion(s) of interest. As noted previously, the ultrasonic image(s) provide an indication of the elasticity of the lesion tissue and from this elasticity information a further determination of the durability of the lesion as a conduction block may be clinically made.

Figure 2A:
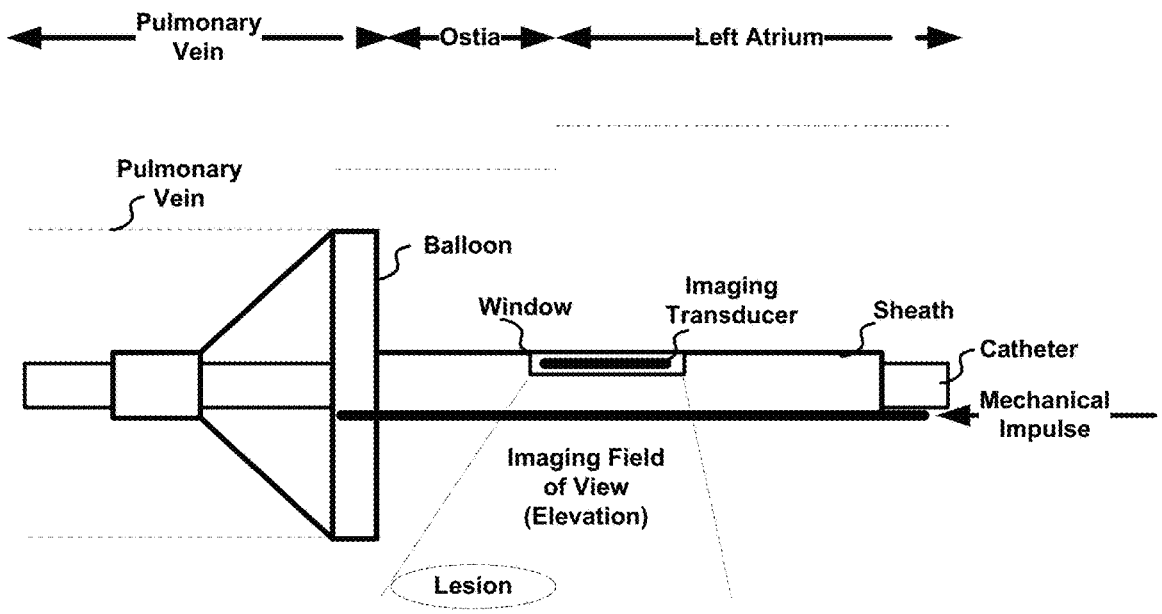
FIG. 2(A), and FIG. 2(B) are schematic diagrams of the illustrative imaging catheter and arrangement for lesion evaluation as a side view (FIG. 2(A)) and simplified 3D view (FIG. 2(B)) wherein the catheter is anchored through the effect of an inflatable balloon and impulse(s) are provided from outside the balloon according to aspects of the present disclosure.
Figure 2B:
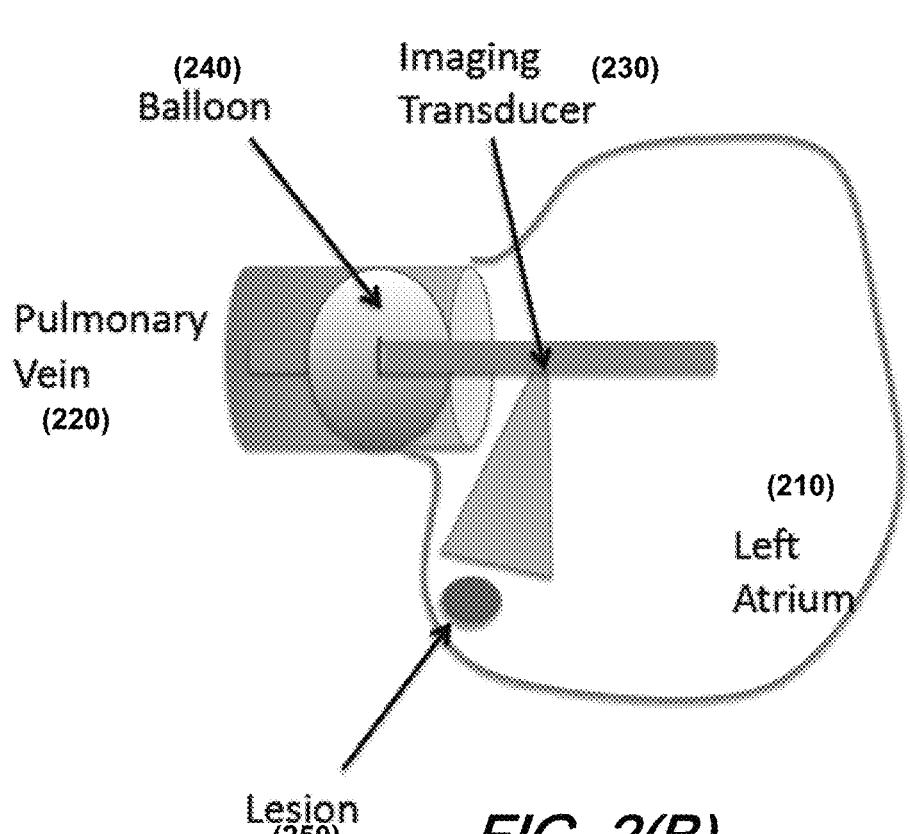

With simultaneous reference now to FIGS. 2(A) and 2(B), there are shown schematic diagrams in side view and simplified 3D view of an illustrative imaging catheter arrangement 200 that advantageously facilitates elasticity imaging for lesion evaluation according to aspects of the present disclosure. As illustratively depicted in that figure, a pulmonary vein 220 is shown entering the left atrium 210 of a heart via the pulmonary vein ostia of the atrium. Illustratively shown positioned within the vessel is an electrocardiography (ICE) imaging catheter including having an inflatable balloon 240 positioned at a distal end of the catheter and an imaging array/transducer 230 located proximal to that balloon.

As is known in the art, a catheter-tipped miniaturized echo transducer may employ a series of crystals (i.e., phased arrays) or a single crystal in which a beam is moved by mechanical means around a circle. Phased array systems employ either linear phased arrays—sector shaped images with side-firing arrays—or circular phased arrays—radially arranged crystals around the tip of the catheter with a circular image format.

Returning to our discussion of FIGS. 2(A) and 2(B), we noted that the catheter arrangement of the present disclosure further includes a balloon positioned on the catheter such that when the catheter is inserted into a blood vessel (in this illustrative example the pulmonary vein) and the balloon is sufficiently inflated the catheter assembly is then anchored within the blood vessel.

We note that those skilled in the art will readily appreciate that there are a number of ways that the balloon—or balloons—may be sufficiently positioned on/within the catheter such that upon inflation the catheter becomes anchored within the blood vessel into which it is inserted. Since the catheter is substantially a long, tubular structure, one or more balloons may be positioned on an exterior surface of the catheter. The balloon(s) may be further positioned around a perimeter of the catheter for subsequent inflating during/after insertion. Finally, one or more of the balloons may be positioned within the body of the catheter during insertion—wherein the catheter includes one or more openings in its body such that a balloon will emerge from the body upon inflation. Depending upon the configuration employed, the balloon(s) may be held in place on/in the catheter/sheath by a suitable adhesive or mechanical structure.

As may be understood and appreciated, the one or more balloon(s) may be fabricated from any of a variety of known materials including flexible polyvinyl chloride (PVC), cross-linked polyethylene, polyethylene terephthalate (PET), nylon, polyurethane, silicone, or other materials including natural and/or synthetic "rubber" or other material(s) that are suitably inflatable and bio-compatible. Furthermore, such balloon(s) may be coated with other materials including those for lubrication and/or abrasion resistance. Still further, such balloons and materials may be composites—for example—balloons having different material compositions including those which limit the size of any inflation or those that promote the expansion/inflation of the balloons in one direction preferable to another direction. For example, balloons may be constructed to expand easily radially, followed by axial expansion—that is to say, side walls of the balloon would be stiffer.

Such balloons may be fabricated either with a change in material or change in material properties. As such, portions of the balloon substantially parallel to a catheter body would be a low(er) durometer flexible material such as polyurethane or silicone, while the sides perpendicular to the catheter may be a high(er) durometer stiff material such as PET or nylon.

Operationally—and as illustrated in the figure—the ICE imaging catheter including balloon(s), is inserted into the pulmonary vein and the balloon(s) is/are inflated to secure/anchor the structure in place. Once anchored, the catheter may be rotated within the vein to evaluate any lesion(s) 250—that in this illustrative example—are located in the left atrial pulmonary vein ostia.

As may be appreciated and understood, lesions within an imaging distance of the catheter (~2 cm) may be imaged. Because the imaging plan is perpendicular to any lesion(s), to evaluate all parts of a lesion requires circumferential rotation with a small angular displacement of just a few degrees between images. As such, a plurality (>10) images is likely required to interrogate a single vein. Advantageously, and as will be described in greater detail later, the circumferential rotation may be computer controlled, robotically performed and advantageously synchronized with the imaging operation(s).

Note that while not explicitly shown in this figure, an imaging transducer—that which provides the mechanical pulse(s) to the tissue via the inflatable balloon—is presumed to be located remote from the balloon itself. In such a configuration, the pulse generator is preferably external to the body and such pulse may be generated and subsequently conducted via the catheter and/or sheath and/or additional structure that suitably conducts the mechanical impulse.

Figure 3A:
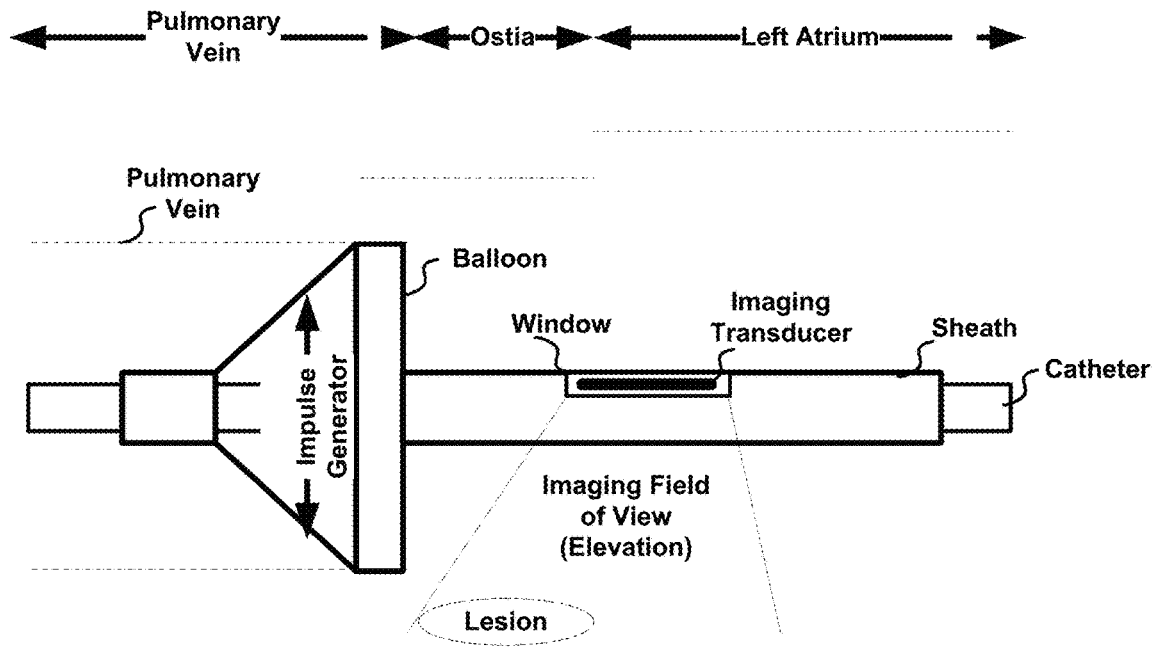
FIG. 3(A) is a side view schematic diagram of the illustrative imaging catheter and arrangement for lesion evaluation wherein the catheter is anchored through the effect of an inflatable balloon and impulse(s) are provided from within the balloon according to aspects of the present disclosure.
Figure 3B:
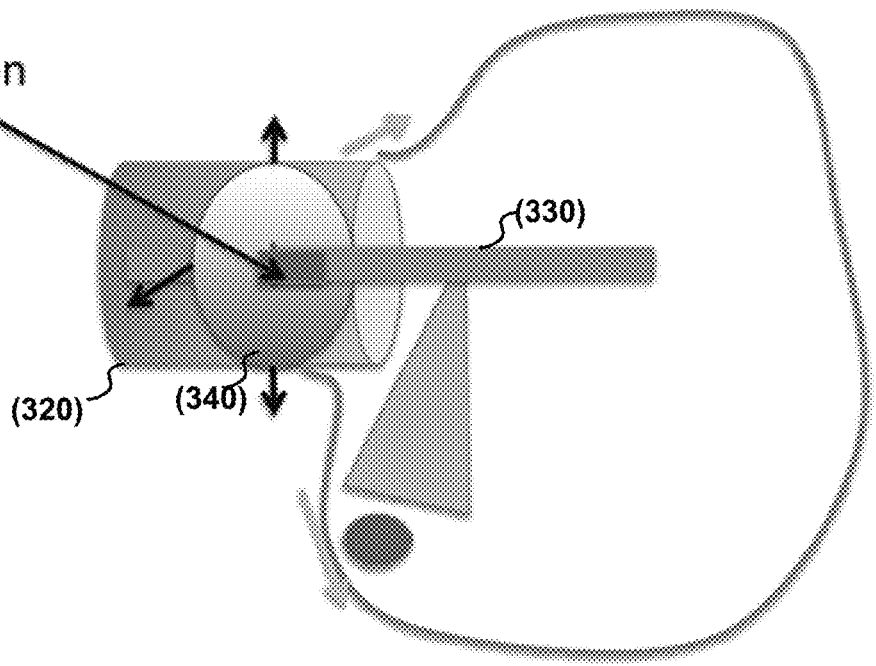
FIG. 3(B) is a simplified 3D view schematic diagram of the illustrative imaging catheter and arrangement for lesion evaluation wherein the catheter is anchored through the effect of an inflatable balloon and impulse(s) are provided from within the balloon according to aspects of the present disclosure.

Turning now to FIG. 3(A) and FIG. 3(B), there is shown a side view schematic (FIG. 3(A)) and simplified 3D diagrams (FIG. 3(B)) showing an illustrative imaging catheter and arrangement for lesion evaluation wherein the catheter is anchored through the effect of an inflatable balloon and impulse(s) are provided from within the balloon according to aspects of the present disclosure. More specifically, an imaging catheter including imaging transducer 330 is shown positioned within the left atrium pulmonary vein and anchored through the effect of the inflatable balloon 340. Shown further is an impulse generation device 360 positioned within the anchor balloon such that upon activation, the impulse generation device generates a mechanical impulse that is conducted to nearby tissues that may be interrogated ultrasonically by imaging transducer 330.

Figure 3C:
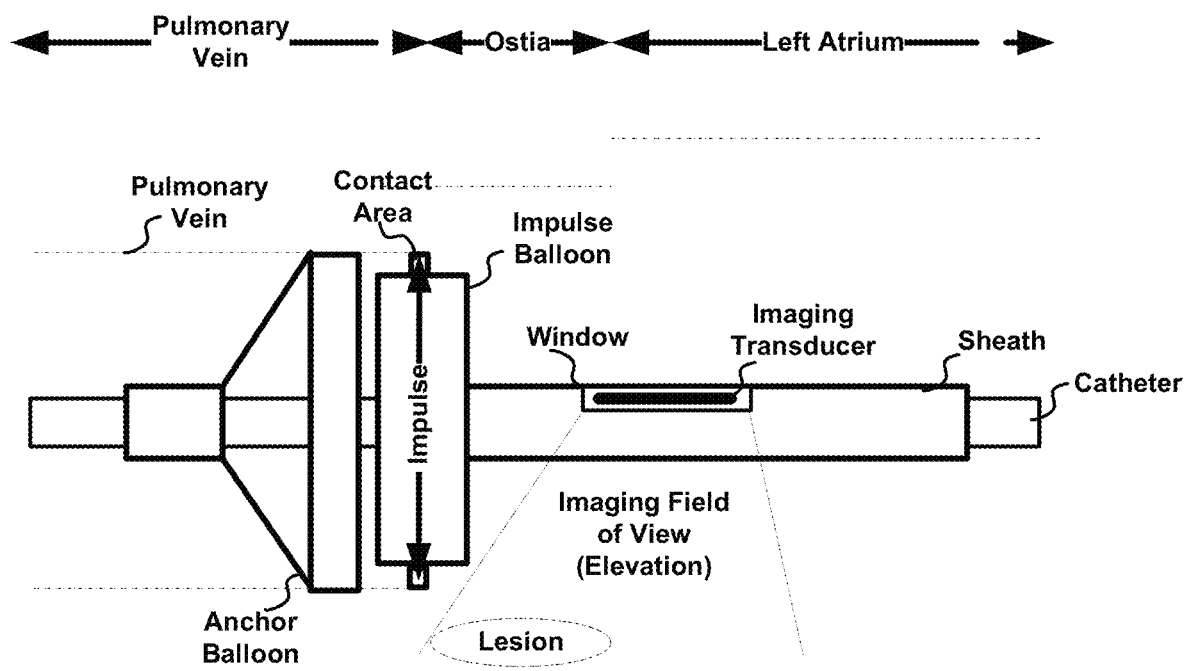
FIG. 3(C) is a schematic diagram of the illustrative imaging catheter and arrangement for lesion evaluation wherein the catheter is anchored through the effect of an inflatable balloon and impulse(s) are provided from a second, impulse balloon according to aspects of the present disclosure.

FIG. 3(C) is a schematic diagram of an illustrative imaging catheter and arrangement for lesion evaluation wherein the catheter is anchored through the effect of an inflatable balloon and impulse(s) are provided from within a separate impulse balloon according to aspects of the present disclosure. As shown in this figure, the impulse balloon 370 is shown positioned between the anchor balloon 340 and the imaging catheter 330. Shown further is that the contact area between the anchor balloon and the pulmonary vein is substantially larger than the contact area between the impulse balloon and the vein.

As will be readily appreciated and as we have determined, a smaller contact area between the impulse balloon and the surrounding tissues results in a more-desirably defined impulse imparted to that tissue. As will be further appreciated the specific amount of contact area may be affected by the nature of the impulse generating device(s) employed and their frequency of operation. Note further that a particular region—for example the "band" of the impulse balloon that contacts the tissue—may be constructed from a material exhibiting different elastic or other properties from other regions of the balloon. In this manner, different materials may be employed to further provide desirable impulse characteristics between the impulse balloon and the surrounding tissue(s). Note further that while not shown previously, such a narrow contact area and/or alternative material structure such as that contemplated may also be employed in the single balloon—anchor/contact—configuration described previously.

We note at this in order to realize long imaging times associated with the number of images that must be acquired, a frame rate—for multiple reasons—is generally limited to the heart rate, or a relatively small—1 to 3—multiple of the heart rate. To accomplish this, a catheter capable of generating 3D sector scan with an elevation is utilized to reduce the number of images needed to perform the 3D ultrasound imaging. Those skilled in the art will readily appreciate that such "elevation" is a type of "field of view" of the imaging probe. As such, a catheter exhibiting an elevation of about 5 degrees to about 50 degrees may be employed. In other embodiments, a catheter exhibiting an elevation of about 10 degrees to about 40 degrees may be employed. In further embodiments, a catheter exhibiting an elevation of about 15 degrees to about 30 degrees may be employed or in still another illustrative embodiment, a catheter exhibiting an elevation of about 20 to 25 degrees may be employed.

Appreciably, when such catheters exhibiting such elevations are employed it directly affects the number of individual scans that must be made in order to capture a full 360 degree set of scans. Obviously, the greater the elevation, the fewer the number of individual scans must be made to image over the full 360 degrees.

Figure 4:
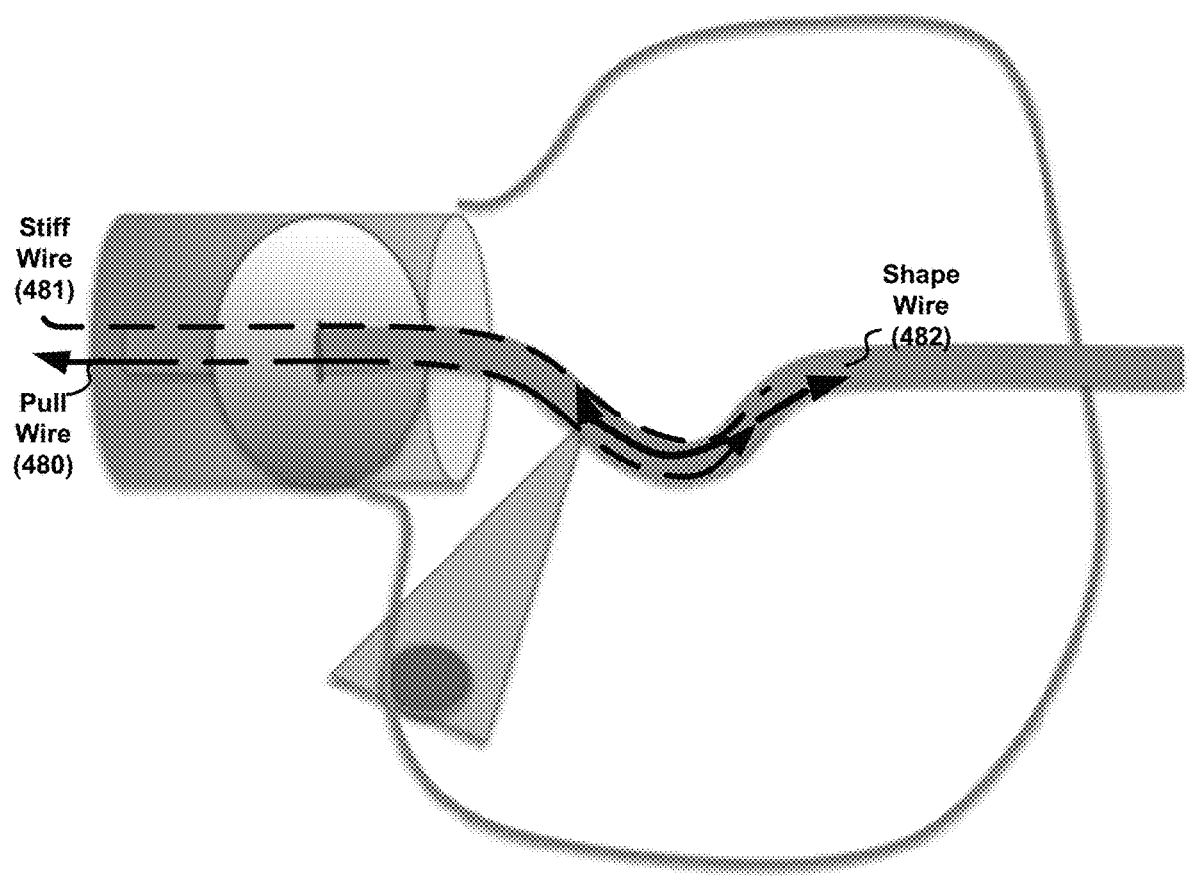
FIG. 4 is a schematic diagram of the illustrative imaging catheter and arrangement for lesion evaluation wherein the catheter is shaped and/or steered with a steering and/or shaped wire such that an improved imaging is achieved according to aspects of the present disclosure.

FIG. 4 is a schematic diagram of the illustrative imaging catheter and arrangement for lesion evaluation wherein the catheter is shaped such that an improved imaging is achieved according to aspects of the present disclosure. As depicted in that figure, the catheter arrangement includes pull wire(s) 480 or other steerable mechanism that runs the length of the catheter and sufficiently anchored to a location of the catheter such that when the wire(s) are "pulled" the imaging angle of the catheter imaging transducer is altered—relative to the tissue being imaged. In this manner, the imaging transducer may be "steered" independently of, or in conjunction with rotation of the catheter. Alternative steering wire mechanisms may be employed including a specialized wire positioned in the region of the imaging transducer. Such wire(s) may include Nitinol wire compositions 482 exhibiting curve(s) that are straightened using a stiff wire 481 during insertion and/or removal.

Operationally, and as will be readily appreciated by those skilled in the art, when a balloon is used to generate and/or conduct the mechanical excitation to the tissue, it effectively delivers a transient volume or pressure pulse to the balloon wall that is contact with the pulmonary vein walls, thereby producing a mechanical wave that propagates along the pulmonary vein and into the left atrium proper—crossing any lesion(s) as it propagates. As the mechanical wavefront encounters any inhomogenity of the lesion(s), there will be a change produced in the magnitude and phase of the mechanical wave. This change is detected by ultrasound imaging/wavetracking technique(s). As will be readily appreciated by those skilled in the art, since wave displacement measurements occur in multiple directions, such imaging employing 3D techniques are beneficial.

As we have already indicated, there exist a number of methods that may be advantageously employed to generate any pressure or volume changes within the balloon(s) employed to impart mechanical impulses to the tissues—according to aspects of the present disclosure. One such method, includes providing a dedicated catheter lumen in pressure/flow communication with a device located outside of the body of the patient. As such, a lumen to inflate the balloon is required and may be employed for delivering the mechanical stimulus. We note that this arrangement—while effective—potentially suffers from modulation of the pressure pulses due to the lumen.

Another impulse generation mechanism includes a ultrasound crystal. Still further impulse generation mechanisms may include photo-acoustic ultrasound generator(s) that employ light and the photo-acoustic effect to generate a transient ultrasound pulse. Still further impulse generating mechanism(s) may include a spark gap that generates a large amplitude pulse.

As those skilled in the art will readily appreciate, such impulse generation mechanisms may be advantageously positioned within the balloon(s) or—in certain applications—within or as part of the imaging transducer itself. We note further that such is the case whether separate impulse balloon(s) are used or whether a single anchor/impulse balloon is employed in a given application.

Note further at this point that in particular applications, a balloon exhibiting localized stiffness characteristics may be employed to enhance desired impulse application. For example, a balloon segment having a reduced stiffness at its maximum radius comprising material(s) and shape properties may be chosen/adjusted to exhibit a non-linear response to a pressure increase. As such, this illustrative balloon structure may be used to generate a higher (spatial) frequency stimulus.

At this point we note that the several lesion evaluation structures described have contemplated one or more balloons (anchor balloon, impulse balloon, dual function anchor/impulse balloon) positioned distal to the imaging transducer. Advantageously structures according to the present disclosure are not so limited.

Figure 5:
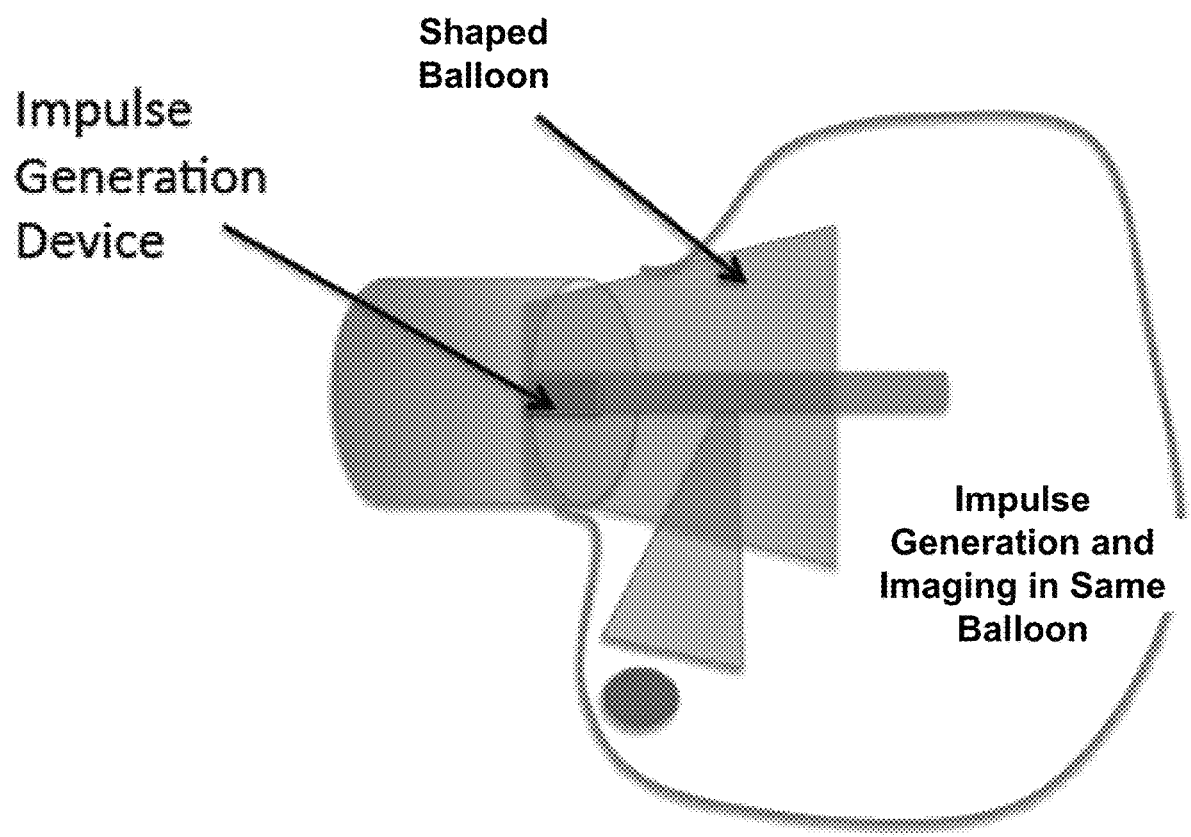
FIG. 5 is a schematic diagram of an alternative, illustrative imaging catheter and arrangement for lesion evaluation wherein the catheter is anchored through the effect of a specifically shaped, inflatable balloon and impulse(s) are provided from within the balloon according to aspects of the present disclosure.

FIG. 5 is a schematic diagram of an alternative, illustrative imaging catheter and arrangement for lesion evaluation wherein the catheter is anchored through the effect of a specifically shaped, inflatable balloon including both mechanical stimulus (impulse) generator and imaging transducer(s). As shown illustratively in this figure, the balloon is substantially conical shaped such that it fits within a natural shape of the pulmonary vein ostia. In such an arrangement, impulse generation and ultrasound imaging are provided from within the balloon.

Figure 6:
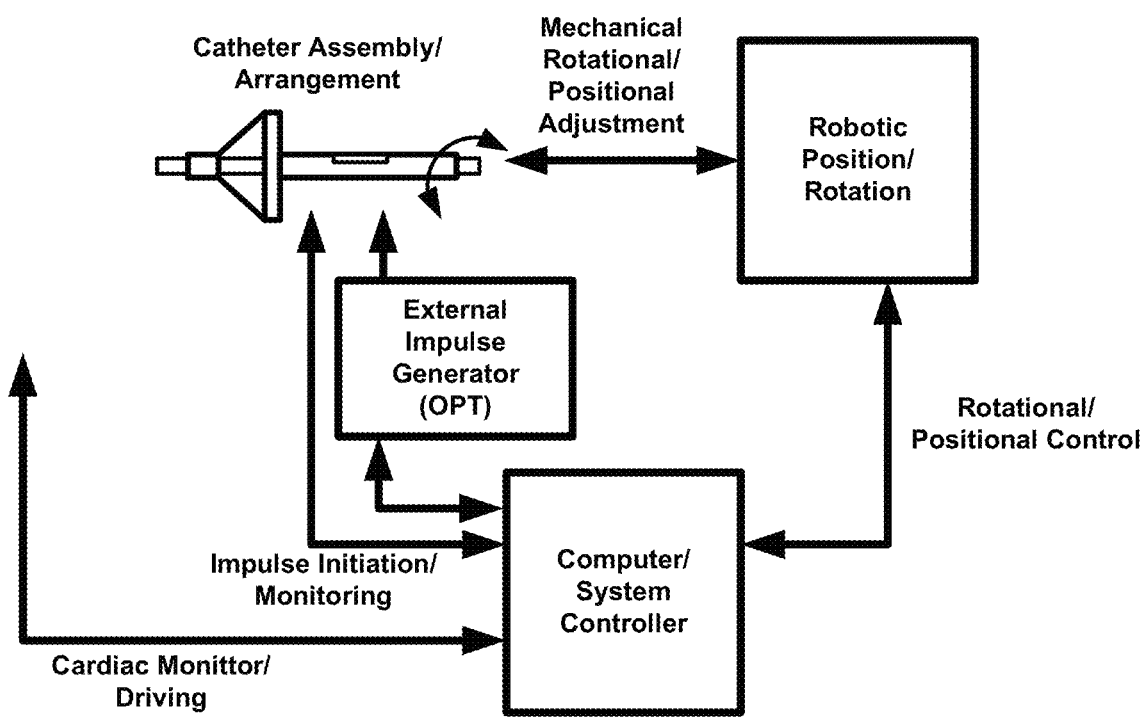
FIG. 6 is a schematic diagram of the illustrative imaging catheter and arrangement for lesion evaluation including control system(s) for initiating/controlling operation and robotic system for rotating catheter during evaluation according to aspects of the present disclosure.

FIG. 6 is a schematic diagram of the illustrative imaging catheter and arrangement for lesion evaluation including control system(s) for initiating/controlling operation and robotic system for rotating/positioning catheter during evaluation according to aspects of the present disclosure. As may be observed from that figure, the catheter assembly arrangement may be positioned/rotated through the effect of a robotic position/rotational system that is optionally under control of an overall computerized system controller. The computer controller advantageously may monitor the catheter and initiate impulses in synchronization with monitored cardiac status. More particularly, the impulse generation may be advantageously synchronized during diastole periods when the heart is refilling and not actively contracting. In this manner, the imaging may be enhanced as the mechanical disturbances induced in lesions under evaluation are only those introduced by the probe impulses, and not normal cardiac activity.

Figure 7:
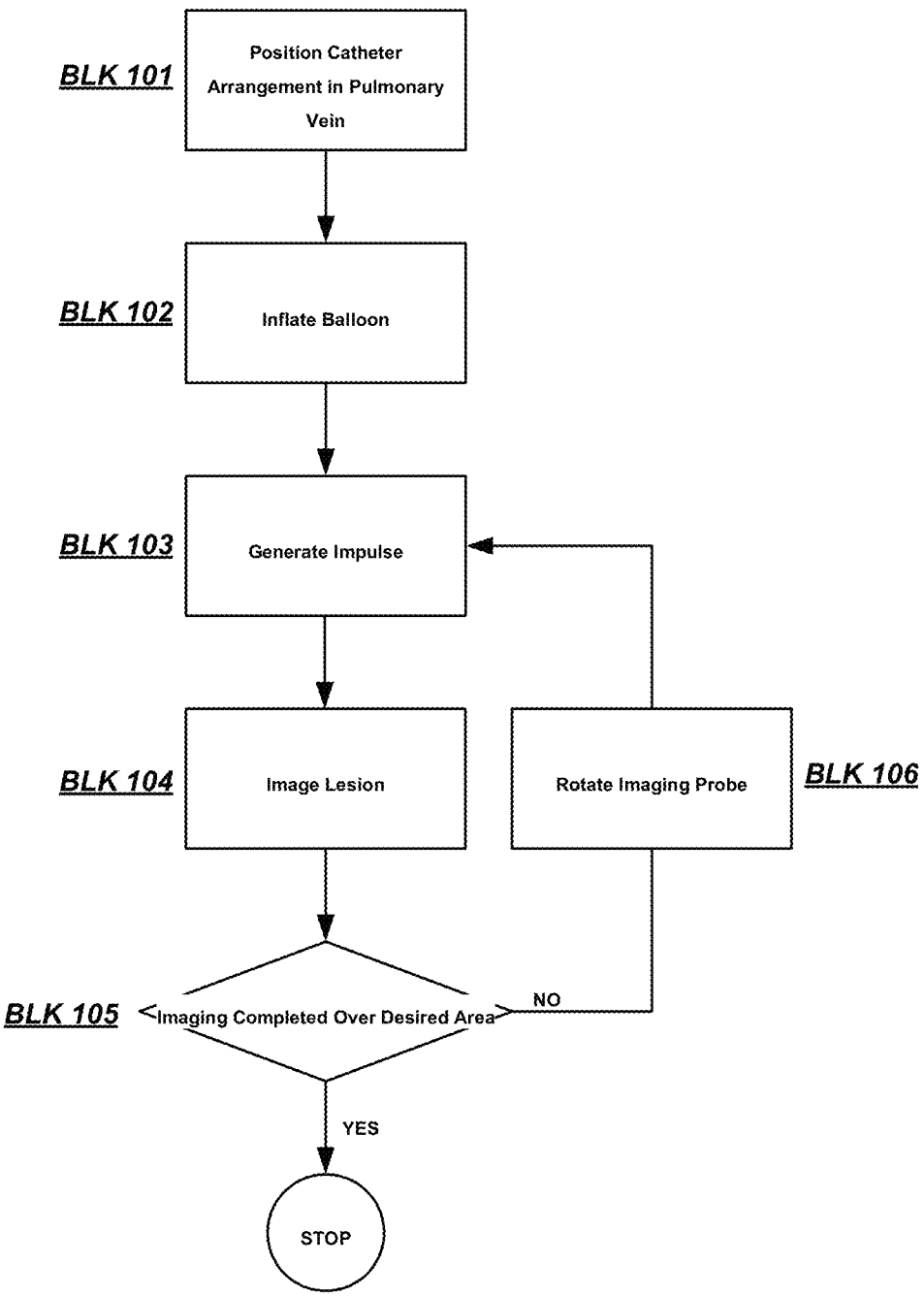
FIG. 7 is a flow diagram of an illustrative method in which an imaging catheter arrangement is inserted into a pulmonary vein, an anchor balloon is inflated to anchor the arrangement in place, imaging a lesion, and subsequently determining a durability of the lesion with respect to its isolation properties—all according to aspects of the present disclosure.

FIG. 7 is a flow diagram of an illustrative method in which an imaging catheter arrangement is inserted into a pulmonary vein, an anchor balloon is inflated to anchor the arrangement in place, imaging a lesion, and subsequently determining a durability of the lesion with respect to its isolation properties—all according to aspects of the present disclosure. By inspection of that figure, it may be observed that at BLK 101 a catheter assembly such as that shown and described herein is inserted at a location in the pulmonary vein such that isolation lesion evaluation may be made. Once position, at BLK 102 the balloon(s) of the assembly are inflated sufficiently to anchor the assembly in position. At BLK 103 an impulse is generated that mechanically excites the lesion tissue and at BLK 104 the lesion is ultrasonically imaged after excitation to determine its elastic characteristics from which a durability determination may be made. Since the lesion(s) may be formed along a full 360 degree circumference of a left atrial pulmonary vein ostia—for example—additional images along that full internal circumference may be made according to BLK 105 and BLK 106 by selective rotation of the assembly. Once the full range of images are made, the process ends and a durability determination may be made from the images so made and collected.

At this point, while we have presented this disclosure using some specific examples, those skilled in the art will recognize that our teachings are not so limited. Accordingly, this disclosure should be only limited by the scope of the claims attached hereto.

The invention claimed is:

1. An imaging catheter structure for isolation lesion evaluation:
an imaging catheter;
a balloon affixed to a distal end of the catheter;
an impulse generator in mechanical communication with the balloon configured such that when the impulse generator is active, mechanical impulses are conducted to the isolation lesion via the balloon; and
a pull wire, a shaping wire and a straightening wire, each of said wires being a distinct wire, said pull wire affixed operable to modify an angle of an imaging transducer with respect to the isolation lesion, said shaping and straightening wires configured such that the imaging catheter adopts the shape of the shaping wire when the straightening wire is adjusted.

2. The structure according to claim 1 wherein the impulse generator is positioned within the balloon.

3. The structure according to claim 2 wherein the impulse generator is one selected from the group consisting of: photo-acoustic impulse generator, a spark-gap impulse generator, and a ultrasound crystal.

4. The structure according to claim 1 further comprising:
a catheter lumen in mechanical communication with the impulse generator and the balloon, said catheter lumen configured to conduct impulses generated by the impulse generator to the balloon.

5. The structure according to claim 1 wherein the balloon has locally increased or decreased stiffness at its maximum radius as compared with other areas of the balloon.

6. The structure according to claim 1 further comprising a second balloon, the second balloon is configured to deliver an impulse to surrounding tissue and the balloon is configured to secure the imaging catheter to tissue.

7. The structure according to claim 1 wherein the balloon is shaped to conform to surrounding tissues and the impulse generator and an imaging transducer of the imaging catheter are positioned within the balloon.

8. The structure according to claim 6 wherein the second balloon exhibits a surface area that contacts surrounding tissue that is smaller than a surface area that contacts surrounding tissue of the balloon.

9. The structure according to claim 1 further comprising a robotic manipulator that mechanically rotates the imaging catheter.

10. The structure according to claim 1 wherein the imaging catheter is configured to generate a 3D sector scan and elevated such that a reduced number of images is needed to perform 3D ultrasound imaging.

11. The structure according to claim 10 wherein the structure exhibits an elevation from about 5 degrees to about 50 degrees.

12. An isolation lesion evaluation method comprising:
positioning an intracardiac imaging catheter within a blood vessel of a patient;
inflating an anchor balloon affixed at an end of the catheter, distal to an imaging transducer positioned in the catheter, such that the catheter is anchored to the blood vessel,
applying a mechanical impulse to the isolation lesion via the anchor balloon; and
providing and operating a pull wire, a shaping wire, and a straightening wire, each of said wires being a distinct wire, said pull wire affixed operable to modify an angle of an imaging transducer with respect to the isolation lesion, said shaping and straightening wires configured such that the imaging catheter adopts the shape of the shaping wire when the straightening wire is adjusted.

13. The method according to claim 12 further comprising: imaging the isolation lesion subsequent to the application of the mechanical impulse.

14. The method according to claim 13 further comprising: rotating the imaging catheter by an amount about its central axis.

15. The method according to claim 14 further comprising: determining a durability characteristic of the isolation lesion.

16. The method according claim 13 further comprising: manipulating a pull wire to modify an angle of an imaging transducer with respect to the isolation lesion.

17. The method according to claim 13 wherein said imaging is performed during periods of cardiac diastole.

18. A computer-controlled system for evaluating isolation lesions, said system comprising:
   an intracardiac imaging catheter including an imaging transducer;
   a balloon affixed at an end of the catheter, distal to an imaging transducer positioned in the catheter, said balloon sufficiently inflated such that the catheter is anchored to an internal structure of a patient;
   a mechanical impulse generator configured to provide a mechanical impulse to the isolation lesion via the anchor balloon;
   a pull wire, a shaping wire and a straightening wire, each of said wires being a distinct wire, said pull wire operatable to modify an angle of an imaging transducer with respect to the isolation lesion, said shaping and straightening wires configured such that the imaging catheter adopts the shape of the shaping wire when the straightening wire is adjusted;
   a control computer which when programmed and executed causes the system to:
      operate the mechanical impulse generator such that the lesion(s) are mechanically excited;
      operate the imaging transducer to collect an ultrasonic image of the excited lesion.

19. The system according to claim 18 further comprising a robotic manipulator mechanically coupled to the imaging catheter and configured to rotate the catheter upon activation, wherein the computer is further programmed and upon execution causes the system to:
   successively rotate the imaging catheter after the collection of the ultrasonic image until a series of images representing a full 360 degree view of the lesion is imaged.

20. The system according to claim 19 wherein the computer is further programmed and upon execution causes the system to:
   monitor cardiac activity such that any lesion(s) are only mechanically excited during periods of cardiac diastole.

21. The system according to claim 20 wherein the computer is further programmed and upon execution causes the system to:
   determine a durability characteristic of the lesion; and
   output an indicia of that durability determination.

* * * * *